United States Patent [19]

Greenbaum

[11] Patent Number: 5,469,229
[45] Date of Patent: Nov. 21, 1995

[54] MULTI-PURPOSE PROTECTIVE EYE SHIELD

[76] Inventor: Steven S. Greenbaum, 35 Haymarket La., Bryn Mawr, Pa. 19010

[21] Appl. No.: 885,715

[22] Filed: Mar. 20, 1992

[51] Int. Cl.⁶ .............................. G02C 7/08; G02C 7/10
[52] U.S. Cl. .................. 351/44; 351/57; 351/60; 351/118; 351/125; 2/15
[58] Field of Search ..................... 351/44, 47, 57, 351/58, 59, 60, 118, 125, 158; 2/13, 15, 427, 431, 438, 432

[56] References Cited

U.S. PATENT DOCUMENTS

| | | | |
|---|---|---|---|
| 868,857 | 10/1907 | Garner | 351/59 |
| 1,279,884 | 9/1918 | La Roche . | |
| 1,905,675 | 4/1933 | Baker | 351/59 |
| 2,459,021 | 1/1949 | Frommer | 351/59 |
| 2,978,955 | 4/1961 | Frommer | 351/57 |
| 3,274,614 | 10/1964 | Boyer . | |
| 3,791,722 | 2/1974 | Ahlberg et al. | 351/45 |
| 3,901,589 | 8/1975 | Bienenfeld | 351/47 |
| 4,249,804 | 2/1981 | Stohrer | 351/121 |
| 4,547,909 | 10/1985 | Bell . | |
| 4,556,995 | 12/1985 | Yamamoto | 2/439 |
| 4,621,378 | 11/1986 | Hatchman | 2/9 |
| 4,630,321 | 12/1986 | Sagemuehl et al. | 2/426 |
| 4,647,165 | 3/1987 | Lewis | 351/59 |
| 4,701,965 | 10/1987 | Landis | 2/428 |
| 4,785,481 | 11/1988 | Palmer, III et al. | 2/436 |
| 4,810,081 | 3/1989 | Mapelli et al. | 351/57 |
| 4,843,643 | 7/1989 | Parissenti et al. | 2/13 |
| 4,901,374 | 2/1990 | Van der Woude | 2/453 |
| 4,924,526 | 5/1990 | Parissenti et al. | 2/13 |
| 4,965,887 | 10/1990 | Paoluccio et al. | 2/9 |
| 5,016,292 | 5/1991 | Rademacher | 2/431 |

FOREIGN PATENT DOCUMENTS 0300384  1/1989  European Pat. Off. ............. 351/57

OTHER PUBLICATIONS

Photo of eyeglasses with accompanying brochure from USA Sport.

Epstein, Ernst, "Magnifiers in dermatology: A personal survey", SSG, File 13, No. 4, Oct. 1985 PT 687–698.

Primary Examiner—Ricky D. Shafer
Attorney, Agent, or Firm—Ratner & Prestia

[57] ABSTRACT

A multi-purpose protective eye shield having a main lens and at least one auxiliary lens attached to a universal frame which includes two temple bars and a nose support element. The frame may include a connecting bridge extending along the brow of the wearer. The auxiliary lenses are each individually coupled to the universal frame or the main lens. Associated with each auxiliary lens are individual hinges, for rotating the lenses about the hinge axis.

14 Claims, 10 Drawing Sheets

MULTI-PURPOSE PROTECTIVE EYE SHIELD

BACKGROUND OF THE INVENTION

This invention pertains to protective eye and face shields. In particular, this invention is a multipurpose protective eye shield for protecting the mucous membranes of the eyes, nose and mouth from physical contaminants, improving vision of the wearer, and/or preventing exposure of the wearer's eyes to possibly dangerous levels of radiation.

In many fields, there is a need for an eye shield which can protect the wearer from both physical contamination and from radiation. For example, medical doctors, dentists, nurses, pharmacists, laboratory workers, electricians, welders, painters, policemen, and firemen are among some of the people who require shields for protection from flying debris, contaminants, and/or radiation.

Furthermore, it would be useful to have a shield which is capable of magnification or which is capable of correcting the wearer's vision. In addition, it would be useful to easily interchange lenses on a face shield to achieve the various purposes as needed. For example, a wearer might selectively need, first, a magnification lens and then an ultraviolet radiation protective lens over a short period of time. For this reason, the various lenses should be able to be used in any combination, as needed, and should be conveniently removed from the eye shield, or from the wearer's line of vision, when no longer needed.

The use of lasers is becoming more widespread in many fields, particularly in fields of medicine and dentistry. The use of lasers can frequently cause dangerous levels of emission of radiation, which may be harmful to the vision of those nearby. Thus, it would be convenient to have a protective eye shield which is adaptable to include a lens for filtering various types of radiation, depending on the particular need.

Specifically in the medical field, safety eye glasses are used to protect the mucous membranes of the eyes, nose, and mouth to prevent the spread of contagious diseases. All devices worn by doctors and other hospital staff should be sterile. Therefore, there is a need for a protective eye shield which is autoclavable.

More generally, protective eye shields should not easily fog when the wearer perspires or the temperature of the surrounding atmosphere changes.

Therefore, to satisfy the variety of needs left unmet by existing protective eye and face shields, a new, multi-purpose, protective eye shield is provided which can protect, improve vision, and prevent exposure to radiation.

SUMMARY OF THE INVENTION

This invention is a shield for protecting the eyes and surrounding area of a wearer. It includes two temple bars each having a rounded ear piece for resting on the ears of the wearer, a main lens connected to the other end of the temple bars and having a top edge extending along the brow of the wearer, and at least one interchangeable auxiliary lens. A coupler engages the interchangeable auxiliary lenses to the top edge of the main lens and hinges are individually associated with each of the auxiliary lenses for rotating the auxiliary lenses. The hinges, each individually associated with an auxiliary lens, can lock the auxiliary lens at rotated positions of 0°, 90°, 135° and 180°. The lenses may serve a variety of purposes, including magnifying or correcting the wearer's vision, preventing physical contaminants from contacting the wearer's eyes and surrounding area, and filtering various types of radiation.

According to another embodiment of the invention, the protective shield includes an inflatable bladder coupled to and surrounding the periphery of the main lens. A hand pump, in fluid communication with the bladder and attached to one of the temple bars, serves to inflate the bladder to a size sufficient to cover and contact the face and forehead of the wearer. This inflated bladder better prevents the passage of physical contaminants from and to the wearer.

According to still another embodiment of the invention, the protective shield has a connecting bridge which connects the non-rounded ends of the temple bars and extends along the brow of the wearer. A nose support extends downwardly from the connecting bridge and rests on the nose of the wearer. Also connected to the connecting bridge is an outwardly extending projection bar having a coupler which couples a main lens to the connecting bridge. A hinge is connected to the coupler for rotating the main lens about the horizontal axis of this hinge. The connecting bridge also receives another coupler for attaching auxiliary lenses to the shield. The auxiliary lenses are hinged for rotational movement about the horizontal axis of the hinge.

BRIEF DESCRIPTION OF THE DRAWING

The invention is best understood from the following detailed description, when read in connection with the accompanying drawings, in which.

DETAILED DESCRIPTION OF THE DRAWINGS

This invention is a-shield for protecting the eyes and surrounding area of a wearer. The invention serves a variety of purposes including protecting the wearer from physical contaminants, correcting or magnifying the wearer's vision, and/or filtering out possible harmful radiation.

Each lens serves one of these unique purposes, and can be easily removed from the wearer's line of vision or, in the case of an auxiliary lens, easily detached from the protective eye shield. In all of the embodiments of the present invention, only the outermost auxiliary lens can be rotated individually and removed from the wearer's line of sight. Other auxiliary lenses may be rotated, but all lenses further away from the wearer than that lens must be rotated as well. Thus, the wearer must be cognizant of the positioning of the lenses, placing the most likely lenses to be removed from the line of sight progressively further away from the wearer. Additionally, physical laws of optics may dictate lens positioning. For example, a corrective lens or a magnifying lens may be required to be positioned a certain distance away from the eyes of the wearer.

The "surrounding area" of the wearer's eyes includes at least the eyes and immediate adjacent area such as the eye brows and upper cheeks. The "surrounding area" may also include the rest of the face, neck and forehead in some cases.

Figure 1:
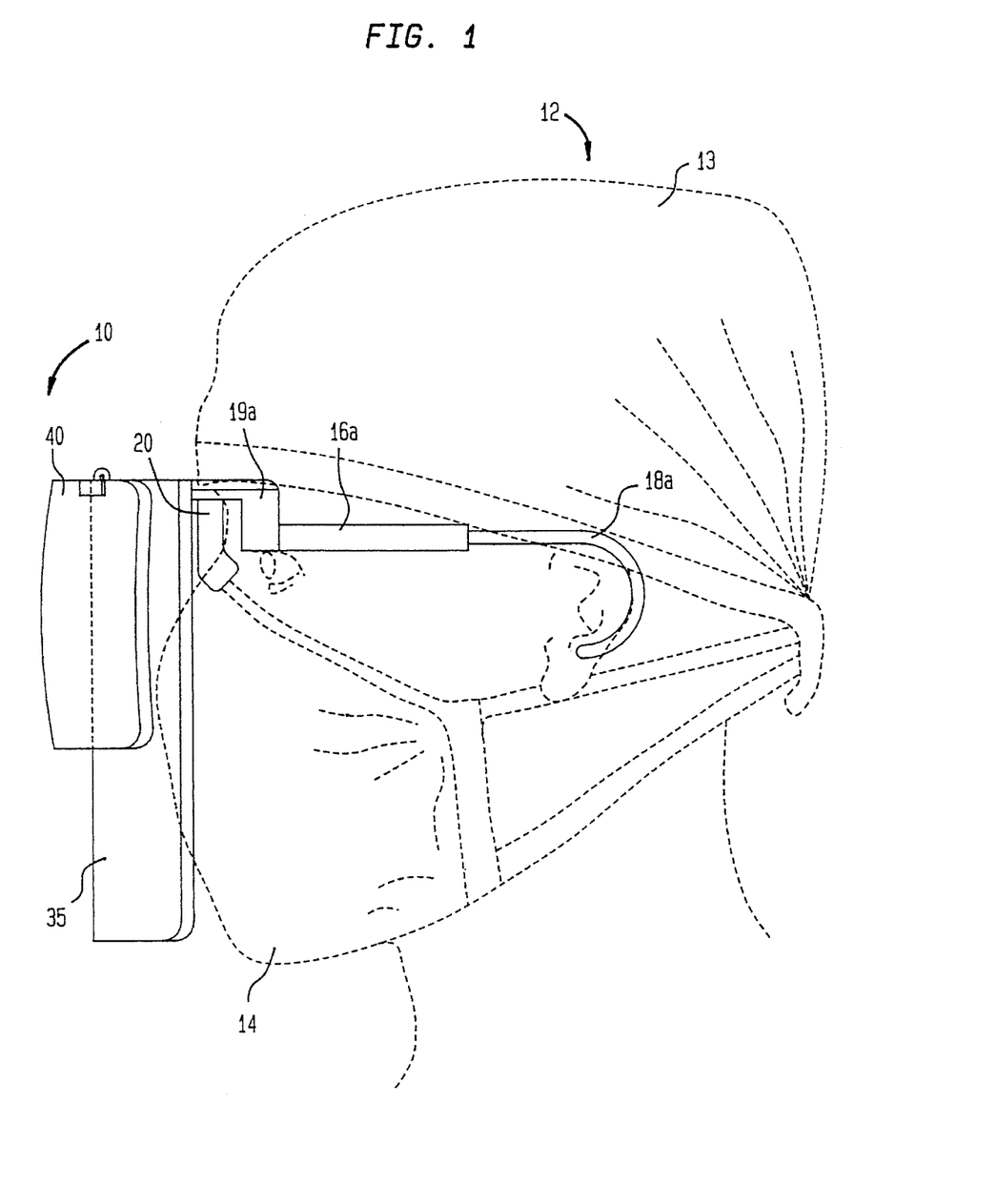
FIG. 1 is a side view showing one embodiment of an eye shield of the present invention being worn by a wearer.

FIG. 1 shows one embodiment 10 of a protective eye shield of the present invention as worn by a wearer 12. In this case, the wearer's occupation is in the medical field as evidenced by the surgical cap 13 surrounding the wearer's head and the surgical mask 14 surrounding the wearer's nose and mouth. Although the protective shield may be worn along with surgical garb, the protective shield may be worn without surgical cap 13, mask 14, or other surgical garb. For example, the protective shield may be worn and used by dentists, electricians, policemen, firemen, laboratory workers, and the like. The shield should be of a material able to withstand an autoclave for sterilization, such as light-weight aluminum or autoclavable plastic. The lenses are also preferably scratch-resistant and light-weight.

Figure 2:
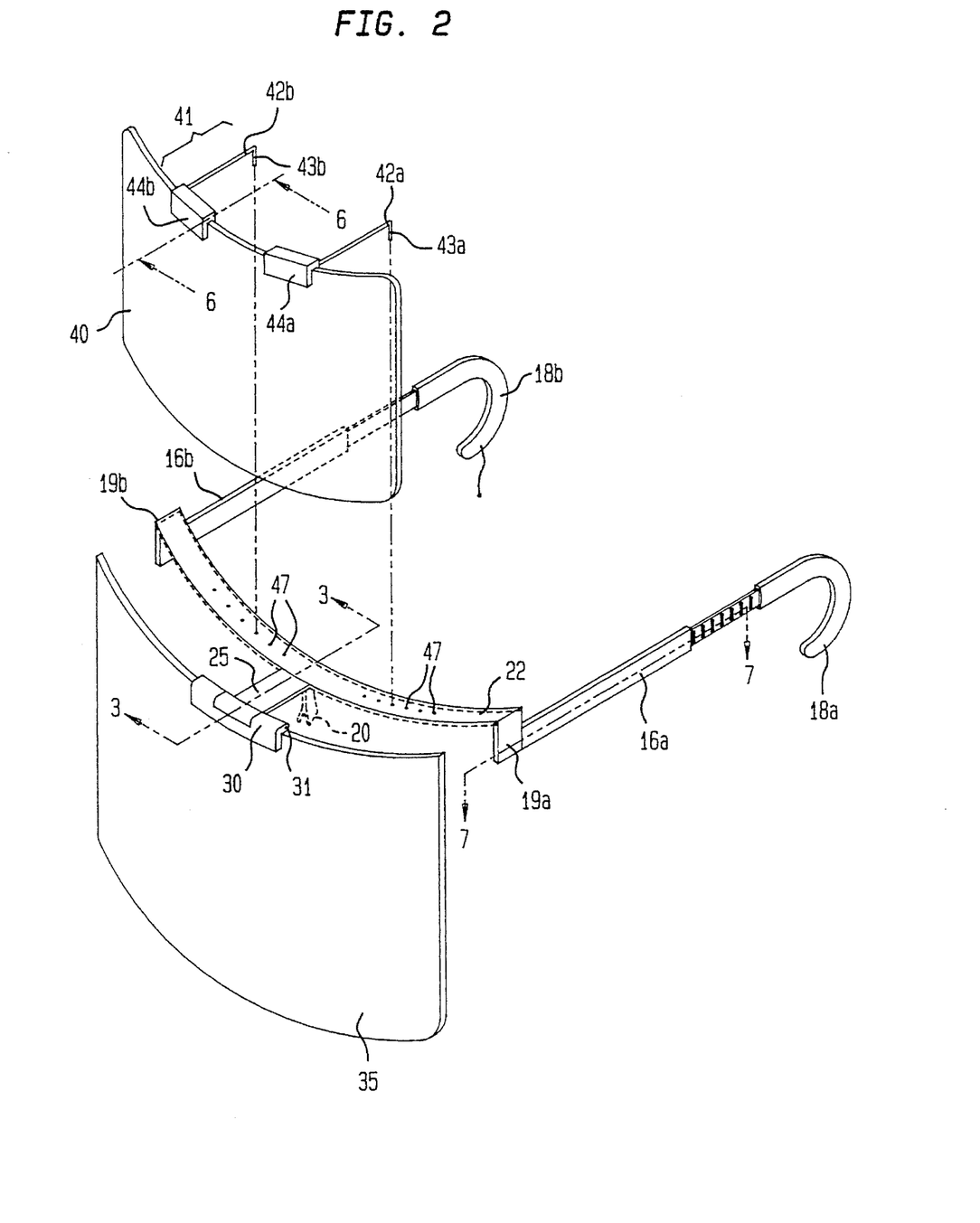
FIG. 2 is a partially exploded perspective view of the embodiment shown in FIG. 1.

As shown in FIGS. 1 and 2, the protective shield is made up of two temple bars 16a and 16b, each having at one end a curved earpiece 18a, 18b, adapted for resting on a wearer's ear as shown by the dashed lines in FIG. 1. The temple bars may either be a rigid material, such as metal, or a more resilient material, such as a hard rubber. Furthermore, the temple bars 16a, 16b, and particularly curved earpieces 18a, 18b, may be coated with a smooth, soft material for comfort. The material used for curved earpieces 18a, 18b is sufficiently rigid so that it only need be adjusted initially for a permanent, comfortable fit for a particular wearer.

Figure 7:
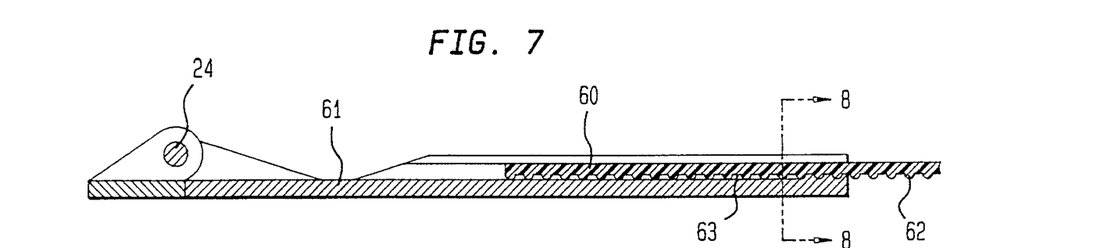
FIG. 7 is an enlarged, detailed cross-sectional view taken along line 7—7 of FIG. 2.

Each temple bar 16a, 16b has at its other end a connecting tab 19a, 19b. Connecting tabs 19a, 19b each include a temple hinge 24 as shown in FIG. 7. This hinge permits relative rotation about the axis of the hinge between the temple bars and their corresponding connecting tabs 19a, 19b. This rotation reduces the storage space required for the protective eye shield because temple bars 16a, 16b can be folded inwardly for storage.

A connecting bridge 22 is attached to the connecting tabs 19a, 19b and extends along the brow of the wearer. Connecting bridge 22 may be of any suitable width and distance away from the brow of the wearer. Connecting bridge 22 is preferably a rigid material.

Figure 5:
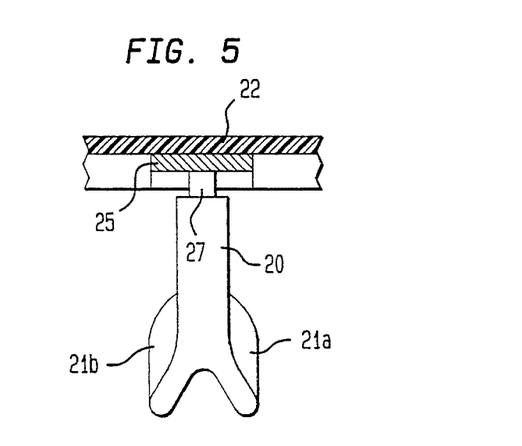
FIG. 5 is a cross-sectional view taken along line 5—5 of FIG. 4.

At the center of connecting bridge 22, a nose support element 20 is firmly attached to connecting bridge 22 and extends downwardly from the connecting bridge. Nose support 20 is adapted to rest on the nose of the wearer as shown in FIG. 1. Nose element 20 includes flanges 21a, 21b, as shown in FIG. 5, which are sufficiently rigid so that they may be adjusted only once initially to conform comfortably to the shape of a particular wearer's nose. The connecting bridge, temple bars, and nose support collectively form a "universal frame."

An outwardly extending projection bar 25 is also rigidly attached to connecting bridge 22 near its center. The planes formed by outwardly extending projection bar 25 and downwardly projecting nose support element 20 may be substantially perpendicular to one another. Alternatively, the planes formed by these two elements may form any angle necessary to permit contact between the nose support element 20 and the nose of the wearer.

As shown in FIG. 5, nose support element 20 includes a coupling pin 27 which may engage an appropriately sized hole in the bottom of outwardly extending projection bar 25. Projection bar 25 may be integrally welded with connecting bridge 22. Alternatively, projection bar 25 may be slidably engaged with connecting bridge 22, so that projection bar 25 may move in a direction from and to the wearer relative to the connecting bridge 22. In this way, the distance between the outer end of projection bar 2B and nose support element 20 may be adjusted as appropriate. By attaching a lens to the outer end of projection bar 25, the distance between the lens and the nose of the wearer may be adjusted. In the event projection bar 25 is welded to connecting bridge 22, there may be a plurality of holes in the bottom of projecting bar 25 so that the nose piece may be adjusted independent of the lens separation distance.

Attached to projection bar 25 at its end furthest away from the wearer (its "outer end") is a main lens coupler 30. Main lens coupler 30 has a conventional hinge 31 extending along a horizontal axis through main lens coupler 30 and the outer end of projection bar 25. Hinge 31 permits rotation of coupler 30 relative to projection bar 25 about its axis. The hinges of this invention are preferably a rust-proof material, such as stainless steel or brass.

Figure 3:
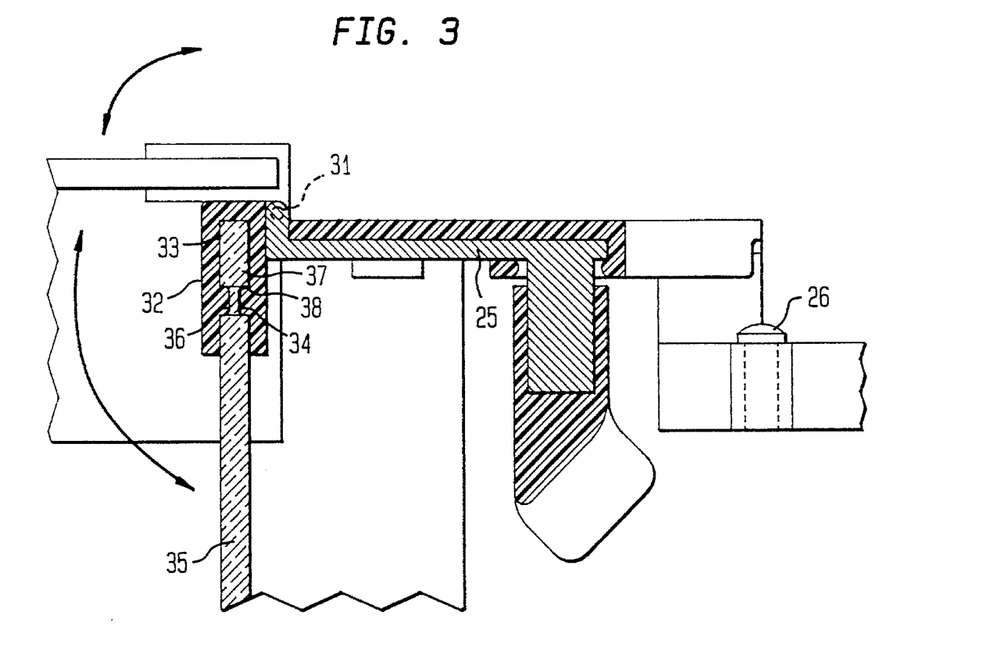
FIG. 3 is an enlarged cross-sectional view taken along line 3—3 of FIG. 2.

Main lens coupler 30 also includes a clamp 32 (shown in FIG. 3) defining an upper bore 33 and a lower bore 34, which form a channel of varying width. Fitted within the channel formed by the bores of clamp 32 is a main lens 35. As shown in FIG. 3, hinge 31 is attached to projection bar 25. As shown by the arrows in FIG. 3, main lens 35 is rotatable about the axis of hinge 31.

Main lens 35 may be any of a number of different types of lenses. For example, it may merely be a clear plastic, plexiglass, or a glass protective shield to prevent physical contaminants to and from the wearer. It may be flat, curved or shaped to need. Also, it may be a magnification lens or a correction lens to suit the particular needs of the wearer. A particular eye correction factor may be ground into the ocular region of the lens. It also may include filters for blocking out harmful radiation from light of varying types and/or wavelengths.

Main lens 35 may contain a narrow section 36 having a width suitable to be fitted within lower bore 34. On the other end of narrow section 36 is attached a widened tip 37. This widened tip has a width suitable to fit within upper bore 33. In this configuration, main lens 35 may be attached to coupler 30 by horizontally sliding the lens into coupler 30 such that widened tip 37 fits within upper bore 33 and narrow section 36 fits within lower bore 34. In this fashion, shoulder 38 which is formed because of the difference in widths of upper bore 33 and lower bore 34, counters the force of gravity and keeps main lens 35 in place.

Figure 3A:
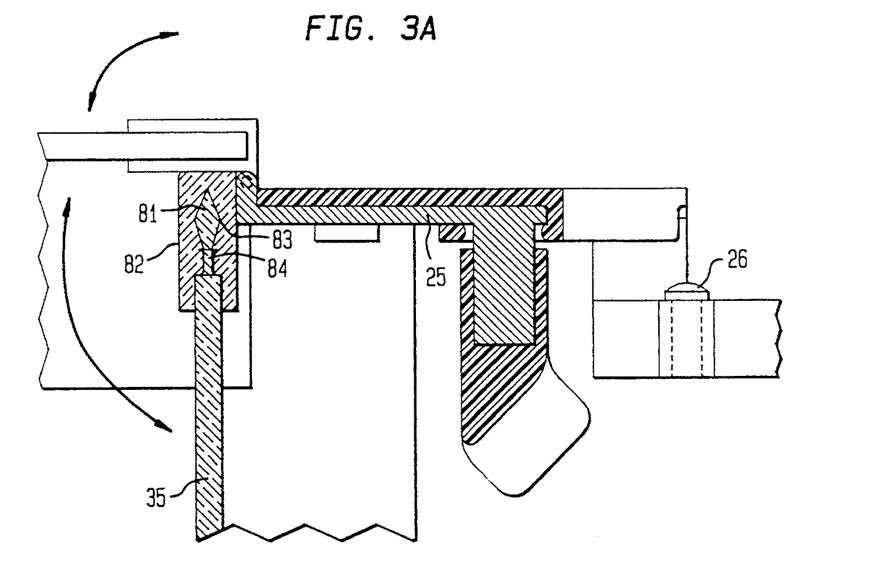
FIG. 3A is the embodiment of FIG. 3 shown including a main lens with a pointed top.

According to another embodiment of the present invention as shown in FIG. 3A, main lens 35 may have a pointed top 81 and clamp 82 may be a pliable material. In this configuration, an upper bore 83 forms a substantially diamond-shaped channel to conform with pointed top 81. To attach main lens 35, the wearer need only drive main lens 35 upward permitting pointed top 81 to pry apart clamp 82 upon insertion. While inserting pointed top 81, the width of bore 84 temporarily increases.

Once main lens 35 is driven sufficiently far upward, clamp 32 will snap together and maintain main lens 35 in place against slight forces, such as the force of gravity. This is achieved because of the resiliency of clamp 82, and the shapes of bore 83 and pointed top 81. This configuration permits easy removal of main lens 35 by pulling downward on lens 35 and prying apart clamp 82. Thus, this configuration provides for easy attachment and detachment of the main lens to clamp 82.

The protective eye shield of the present invention also includes at least one auxiliary lens 40. Auxiliary lens 40 may serve a variety of purposes, similar to main lens 35. Auxiliary lens 40 includes a coupling device which attaches to connecting bridge 22. This coupling device may be any one of known coupling devices for such applications. If so desired, an auxiliary lens may be coupled to the universal frame without a main lens, depending on the particular need.

Figure 4:
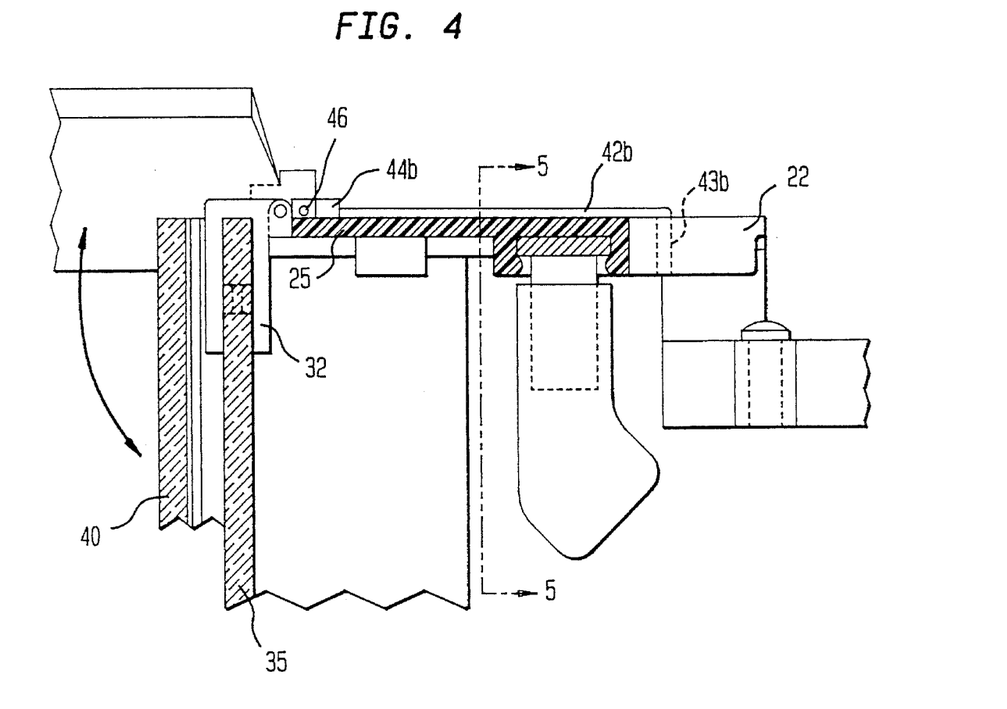
FIG. 4 is the embodiment of FIG. 3 shown including an auxiliary lens.
Figures 6, 8, 9, 10:
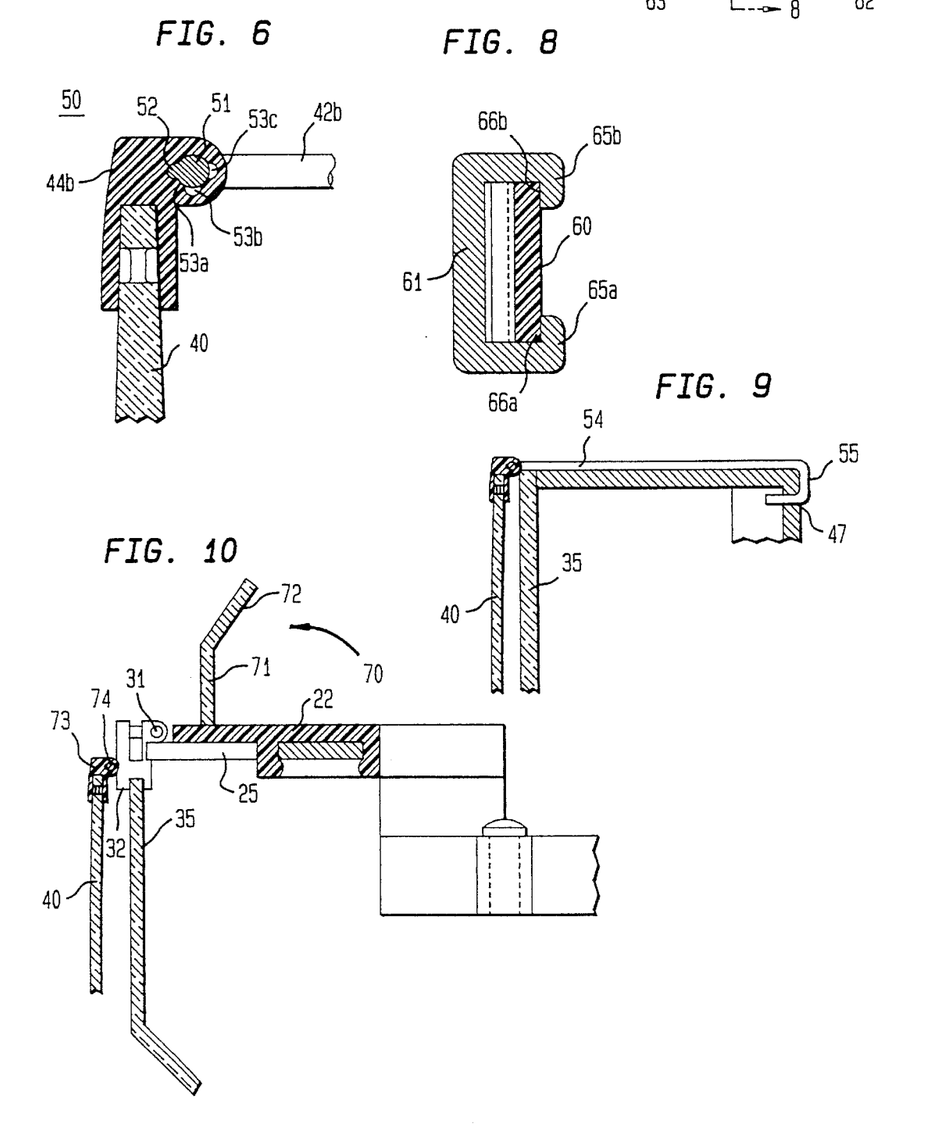
FIG. 6 is an enlarged, detailed cross-sectional view taken along line 6—6 of FIG. 2.
FIG. 8 is an enlarged cross-sectional view taken along line 8—8 of FIG. 7.
FIG. 9 is a cross-sectional view showing a second embodiment of the present invention.
FIG. 10 is a cross-sectional view showing a third embodiment of the present invention.

One coupling device is shown in FIGS. 1, 2 and 4. This auxiliary lens coupler 41 includes mounting pins 42a, 42b which are attached to clamps 44a, 44b. Clamps 44a and 44b may engage auxiliary lens 40 in the same manner that clamp 32 engages main lens 35, as shown in FIGS. 3 or 6. Alternatively, the auxiliary lenses could be permanently affixed to the pins, because the auxiliary lenses could be detached by removing the mounting pins from the connecting bridge. Clamps 44a, 44b each include a hinge, such as hinge 46, shown in FIG. 4. Auxiliary lens 40 is rotatable as shown by the arrows in FIG. 4 about the horizontal axis formed through hinge 46.

As shown in FIG. 4, mounting pin 42b extends from coupler 44b to connecting bridge 22. In one embodiment of the present invention, mounting pins 42a, 42b each have a downwardly projecting end 43a, 43b. In this embodiment, connecting bridge 22 has at least one pair of holes 47, spaced evenly apart from the center of the connecting bridge, for receiving and engaging downwardly projecting ends 43a, 43b of mounting pins 42a, 42b. In this embodiment, downwardly projecting ends 43a, 43b are slightly expandable (or "stress-flexed") for properly engaging holes 47. Squeezing these pins slightly allows them to be inserted into the holes, and their outwardly flexing bias causes them to stay in place.

Alternatively, holes 47 could be formed to include a shoulder for engaging the pins, and mounting pins 43a, 43b could have a pointed bottom for ease of insertion. Also, the mounting pins could include a release lever (not shown) so that the wearer can easily remove the auxiliary lens.

According to a preferred embodiment of the invention, the hinges include a locking mechanism 50 as shown in FIG. 6. For example, this locking mechanism could be a portion of auxiliary lens coupler 41 having a mounting pin 42b and an auxiliary lens 40 as shown in FIG. 6. As shown, the mounting pins include an end extending perpendicularly to the main length of the mounting pins themselves. These ends have an oblong nub 51 having a protrusion 52. Formed within clamp 44b are three recesses 53a, 53b, 53c adapted to receive and engage protrusion 52. When protrusion 52 is locked in one of these recesses, auxiliary lens 40 is positioned at a corresponding angle with respect to the downward-pointing vertical axis. For example, in the embodiment shown in FIG. 6, auxiliary lens 40 is at 0°, 90°, and 180° from the downward-facing vertical axis, as protrusion 52 engages recesses 53a, 53b, and 53c, respectively. Although not shown, smaller recesses and protrusions may be formed into clamp 44a, so that more locking angles may be obtained. Also, more recesses may be formed so that a wider range of angular movement may be obtained for auxiliary lens 40.

According to the second embodiment shown in FIG. 9, a mounting pin 54 similarly attached to auxiliary lens 40 includes a U-shaped end 55. In this embodiment, holes 47 for engaging the mounting pin are at the face of connecting bridge 22 which is closest to the wearer (the "inner face"). Thus, U-shaped end 55 extends over a portion of the inner face of connecting bridge 22. This permits a greater stability with respect to coupling auxiliary lens 40 to the protective eye shield.

FIG. 7 shows one way in which temple bars 16a, 16b may be adjustable. A temple bar may comprise an inner edge 60 and an outer edge 61 as shown in FIG. 7. Inner edge 60 is closer to the wearer and outer edge 61 is further away from the wearer. Inner edge 60 has teeth 62 which engage with teeth 63 of outer edge 61. These teeth may be angled along one edge to form a ratchet effect.

Figure 7A:
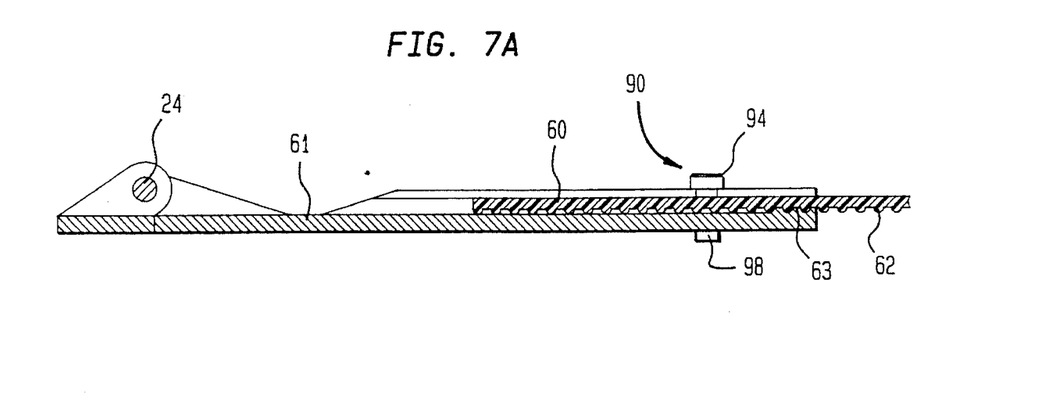
FIG. 7A is the embodiment of FIG. 7 shown including a device for securing the length of the adjustable temple bars.

As shown in FIG. 7A, a tightening device 90 may be provided so that a wearer may more firmly engage the teeth of the two edges once an appropriate length is obtained. The tightening device may be any conventional type of clamp, vise, and the like. As shown, tightening device 90 includes a threaded screw 94 which extends through a plurality of holes (not shown) along inner edge 60 and outer edge 61 and engages a nut 98. In this way, tightening device 90 secures the desired adjustment of the temple bars.

FIG. 8 shows inner edge 60 coupled to outer edge 61. As shown, outer edge 61 includes two tabs 65a, 65b. Tabs 65a, 65b form shoulders 66a, 66b within which is fitted inner edge 60. Inner edge 60 slides along shoulders 66a, 66b so that the wearer can easily adjust the temple bars.

A third embodiment of the invention is shown in FIG. 10. This embodiment includes an extension 70 with a straight portion 71 and an angled portion 72. Extension 70 may be rigidly attached to connecting bridge 22 in a known manner. Alternatively, Extension 70 may be coupled to connecting bridge 22 for easy attachment and detachment. Extension 70 may be used for any or all of the purposes as previously discussed for the main and auxiliary lenses. Also, extension 70 may be opaque. Extension 70 provides protection to the forehead area of the wearer from physical contaminants and/or radiation.

The embodiment shown in FIG. 10 includes a connecting bridge 22, a projection bar 25, a main lens hinge 31 and a clamp 32, which all operate as previously discussed. This embodiment includes an auxiliary coupler 73 which engages auxiliary lens 40 as previously discussed. An auxiliary lens hinge 74 passes through clamp 32. This configuration provides relative rotation between auxiliary lens 40 and main lens 35 about the axis of auxiliary lens hinge 74.

Figures 11, 12, 13:
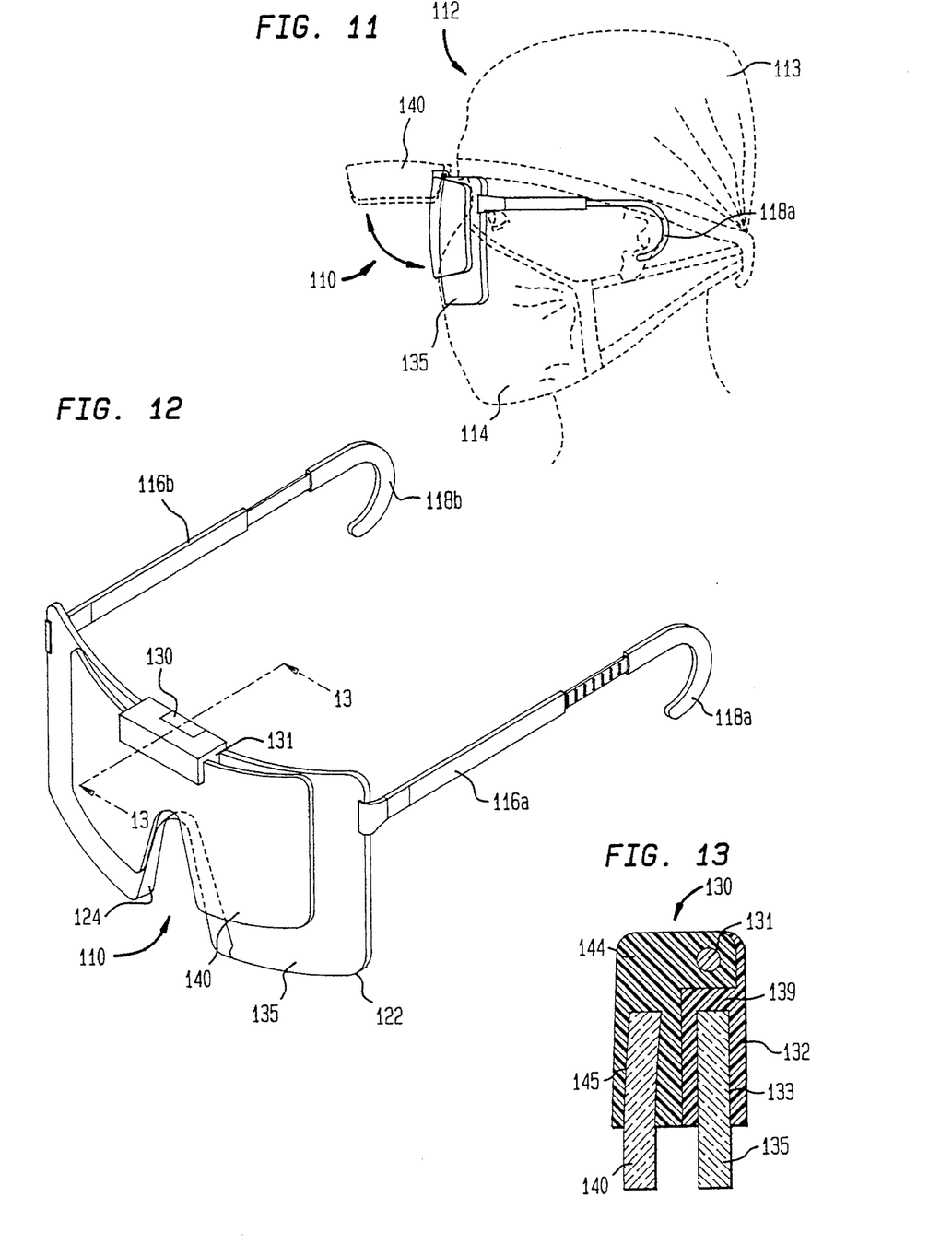
FIG. 11 is a side view showing a fourth embodiment of an eye shield of the present invention as worn by a wearer.
FIG. 12 is a perspective view of the embodiment shown in FIG. 11.
FIG. 13 is an enlarged, detailed cross-sectional view taken along line 13—13 of FIG. 12.

FIG. 11 shows a fourth embodiment 110 of a protective eye shield of the present invention as worn by a wearer 112. As with the previous embodiment, the protective shield may be worn with or without surgical garb 113 and 114.

As shown in FIGS. 11 and 12, the protective shield comprises two temple bars 116a and 116b, each having at one end a curved earpiece 118a, 118b, adapted for resting on a wearer's ear as shown by the dashed lines in FIG. 1. The temple bars are similar in other aspects to those discussed previously in the other embodiments.

A main lens 135 is connected to the temple bars. The main lens 135 may serve a variety of purposes as previously discussed. Main lens 135 includes a top edge 139 extending along the brow of the wearer. Attached to main lens 135 may be a nose support element 124 for resting on a wearer's nose. Main lens 135 may be substantially rectangularly shaped as main lens 35 is shown in FIGS. 1 and 2. Alternatively, main lens 135 may have a bottom edge 122 defining two lobes and a recess with a widened edge 124 adapted for resting on the nose of the wearer.

Attached to top edge 139 of the main lens 135 is at least one coupler 130. One such coupler is shown in FIGS. 12 and 13. This coupler 130 includes a main clamp 132 defining a main recess 133 for engaging main lens 135 in any manner as previously discussed. A conventional hinge 131 is formed within the top of clamp 132 for permitting rotation of a first auxiliary clamp 144 about a horizontal axis along hinge 132. Coupler 130 also defines a recess 145 for engaging a first auxiliary lens 140 in any of the manners previously discussed.

Figure 14:
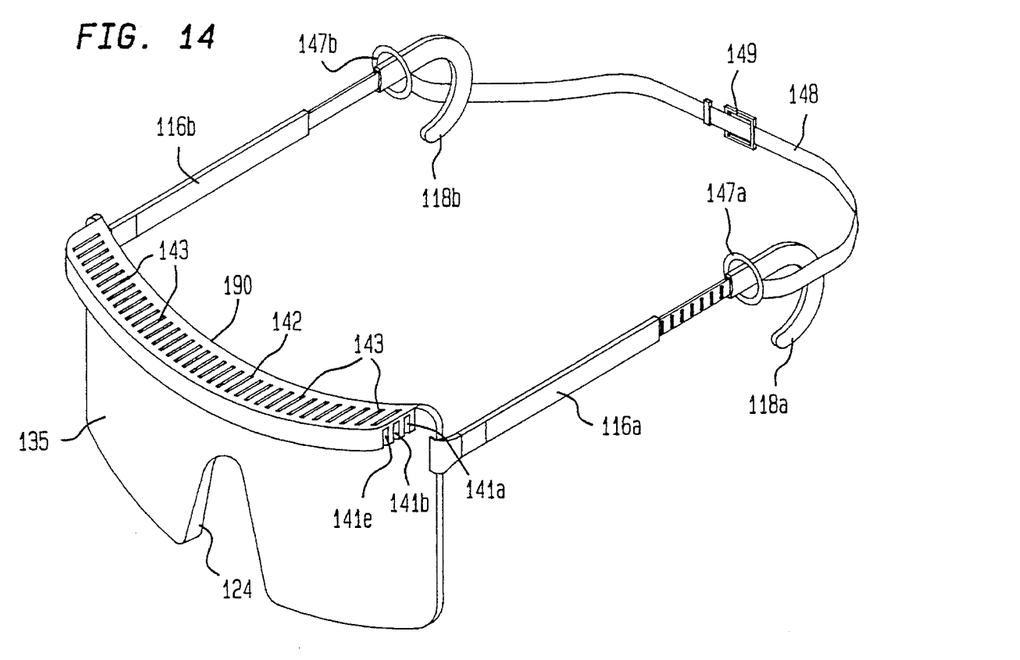
FIG. 14 is a perspective view of a fifth embodiment of the present invention, and showing other aspects of this invention.
Figures 14A, 16:
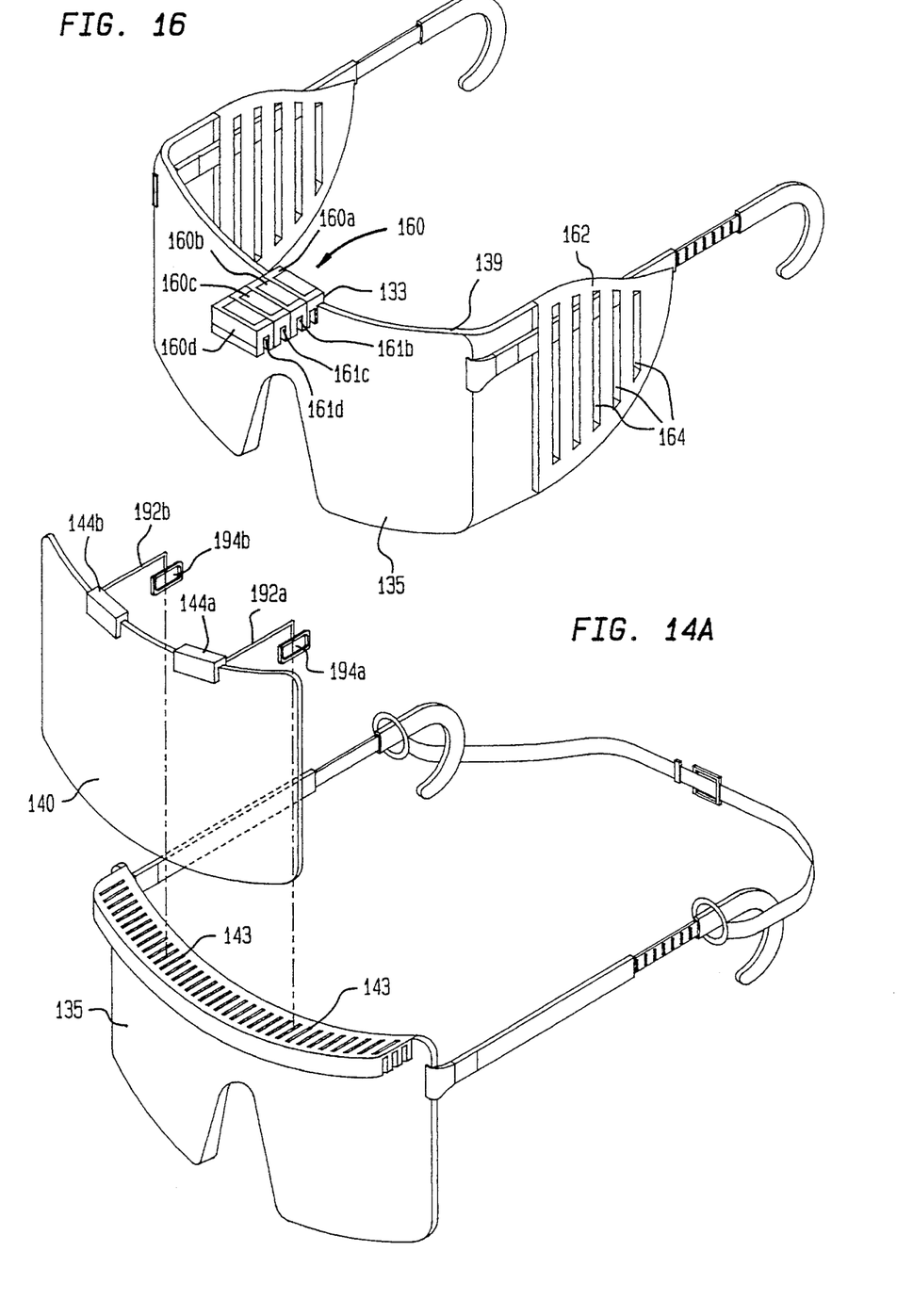
FIG. 14A is the embodiment shown in FIG. 14 featuring another aspect.
FIG. 16 is a perspective view of a seventh embodiment of the present invention, and showing other aspects of this invention.

According to a seventh embodiment of the invention as shown in FIG. 16, coupler 160 includes an outwardly extending projection bar having a main section 160a with a main recess 133 at the first end for engaging main lens 135 and a plurality of auxiliary sections 160b, 160c, 160d having respective recesses 161b, 161c, 161d positioned at varying lengths from main recess 133. Each of these auxiliary recesses is capable of engaging an auxiliary lens.

The seventh embodiment can be described more specifically with reference to FIG. 13. The cross section of the main 160a and first auxiliary section 160b of coupler 160 would be similar to FIG. 13, except that the top of clamp 144 would include a recess adapted to accept another hinge. If a second auxiliary lens were added, this hinge (not shown) from the second auxiliary section 160c would be formed at the not shown recess of the clamp of the first auxiliary section 160b. This hinge would provide for relative rotation between the second auxiliary lens and the first auxiliary lens. Preferably, each individual auxiliary portion is easily attached and detached from the coupler 160 so that the wearer will only have the number of auxiliary portions corresponding to the number of auxiliary lenses needed.

Figure 15:
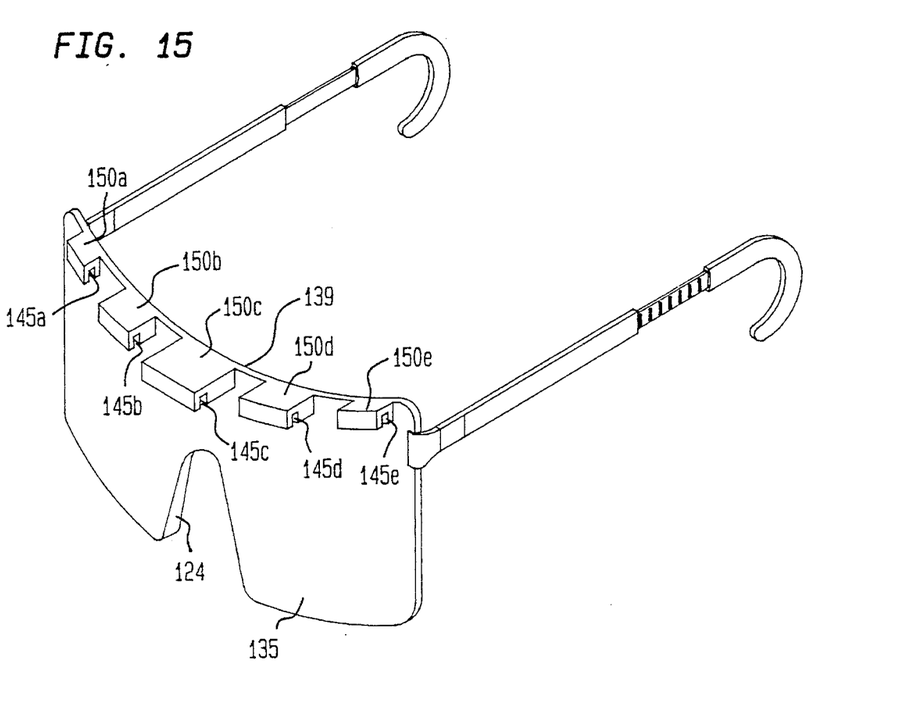
FIG. 15 is a perspective view of a sixth embodiment of the present invention.

According to a sixth embodiment of the invention as shown in FIG. 15, the coupling device is a plurality of couplers 150a–150e. Couplers 150a–150e are outwardly extending projection bars each having a first end attached to the top edge 139 of the main lens 135. Couplers 150a–150e may be rigidly attached to the main lens 135 or may be adapted for easy attachment and detachment to main lens 135. Couplers 150a–150e extend outwardly from the their first ends at varying lengths to a second end. At the second ends of these couplers are devices for engaging auxiliary lenses. For example, recesses 145a–145e of FIG. 15 are positioned at the second ends of couplers 150a–150e, respectively, for engaging auxiliary lenses. Each coupler 150a–150e includes a hinge for rotational movement of the auxiliary lenses as previously discussed.

FIG. 15 includes several possibilities for the uses of the couplers. First, each coupler could extend at a unique length so that each coupler is individually attached to a single auxiliary lens. In this way, five auxiliary lenses could be attached to couplers 150a–150e. Also, more couplers may be attached to the top of main lens 135 as space along the top edge allows.

Second, at least two of the couplers 150a–150e could extend the same length so that an auxiliary lens is engaged by at least two of the couplers. For example, assuming that couplers 150b and 150d extend outwardly the same length, then these two couplers would jointly engage one auxiliary lens.

Finally, all five couplers 150a–150e could be adapted to engage a single, curved auxiliary lens. This would require, in the embodiment shown, couplers 150a and 150e having a relatively short length, couplers 150b and 150d having an intermediate length, and coupler 150c having a relatively long length. In all three of these situations, the auxiliary lenses may be attached to the couplers by any conventional means, including those previously discussed.

According to a fifth embodiment of the invention as shown in FIG. 14, the coupling device is a multiply-grooved connecting bar 190. Connecting bar 190 may connect the two temple bars or may be attached to the top edge of main lens 135. This embodiment includes three ways for engaging auxiliary lenses. The first is similar to those previously discussed and includes downwardly facing clamps, extending along the length of the top edge of the main lens, for engaging auxiliary lenses. These downwardly facing clamps may define recesses 141a, 141b, 141c, which engage the auxiliary lenses in a way similar to the recesses previously discussed. Associated with each of these clamps is a hinge for permitting rotational movement of an auxiliary lens relative to the next inner auxiliary lens. By being "associated with," the hinge is located near the coupler for that auxiliary lens and serves to rotate that auxiliary lens.

The second way in which connecting bar 190 rotatably attaches at least one auxiliary lens is by having a plurality of grooves 143 formed within the top face 142 of connecting bar 190, as shown in FIG. 14A. In this way, each auxiliary lens includes mounting rods 192a, 192b, similar to the mounting pins shown in FIGS. 1, 2 and 4, except with tabs 194a, 194b at the ends of the rods in place of the pins. Tabs 194a, 194b are configured to be rigidly inserted within grooves 143, thereby attaching the auxiliary lenses to main lens 135. At the other end of these mounting tabs may be clamps 144a, 144b similar to clamps 44a, 44b. Formed within these clamps may be hinges, similar to auxiliary lens hinge 46 shown in FIG. 4, for providing rotational movement of the auxiliary lenses about the axis of the hinge.

Figure 14B:
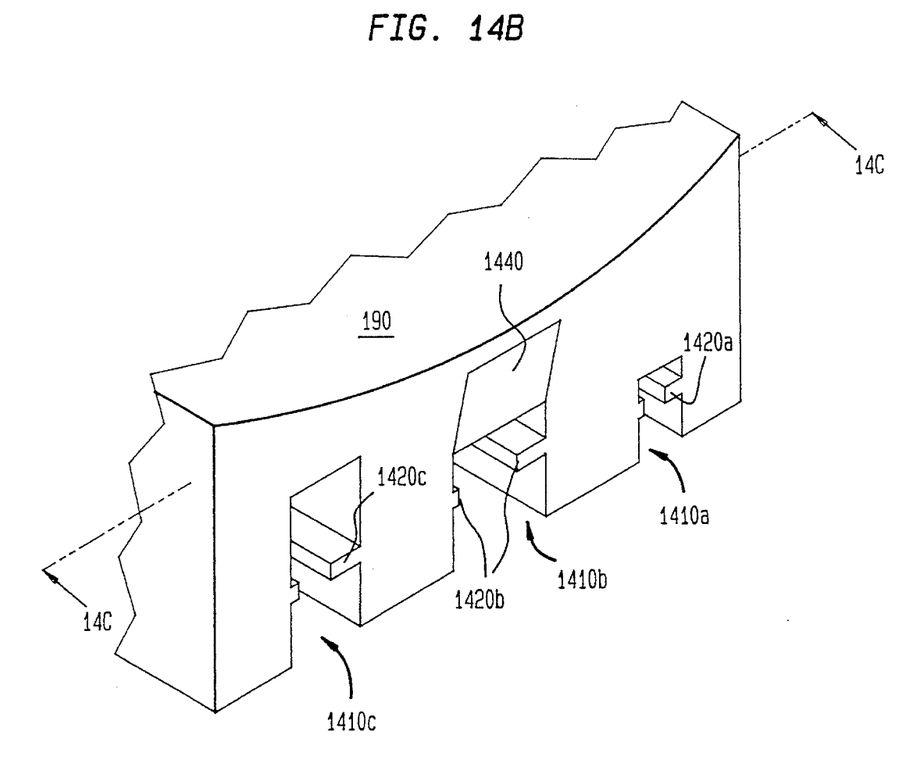
FIG. 14B is an enlarged partial perspective view of the embodiment shown in FIG. 14 featuring still another aspect.
Figure 14C:
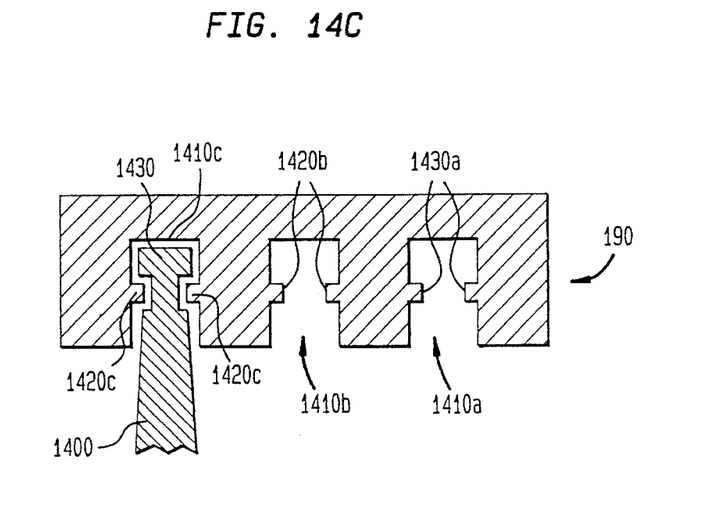
FIG. 14C is a cross-sectional view taken along the line 14C—14C of FIG. 14B.

The third way in which connecting bar 190 rotatably attaches at least one auxiliary lens is by a tongue-in-groove method as shown in FIGS. 14B and 14C. Similar to the first method, downwardly facing clamps define recesses 1410a, 1410b, 1410c. Formed within each clamp are tongues 1420a, 1420b, 1420c which engage grooves formed in an auxiliary lens 1400. Auxiliary lens 1400 includes a widened top 1430 located adjacent the groove for keeping auxiliary lens 1400 attached to connecting bar 190.

In order to couple auxiliary lens 1400 to connecting bar 190, a wearer should slide auxiliary lens 1400 horizontally along the channel formed by one of the recesses 1410a, 1410b, 1410c so that the grooves of auxiliary lens 1400 are engaged by one pair of tongues 1420a, 1420b, 1420c.

A closure element 1440 (shown in FIG. 14B), located at the ends of the channels, ensures that the auxiliary lens does not horizontally slide out of the channel. (A closure element could be located at each end of all channels, but only one is shown for convenience.) Closure element 1440 is adapted to be easily moved by a wearer to an opened position or a closed position. An opened closure element permits the wearer to slide the auxiliary lens into the channel, while a closed closure element prevents the lens from horizontally sliding out of the channel. As shown in FIG. 14B, closure element 1440 is in the opened position.

The eye shield of the present invention may include an adjustable strap 148 as shown in FIG. 14. Strap 148 has resilient loops 147a, 147b for attachment to the temple bars 116a, 116b, preferably to the curved ear pieces 118a, 118b. Strap 148 has an adjustment unit 149 to vary its length. Strap 148 is used to support the protective eye shield on the head or neck of the wearer and for preventing the protective eye shield from falling to the floor in the event that the shield slips from the face of the wearer.

The protective shield may include a tapered side piece 162 as shown in FIG. 16. Tapered side piece 162 may be rigidly coupled to temple bar 116a at one end and the main lens 135 at its other end. This tapered side piece includes vents 164 to permit air to flow into the protective eye piece to prevent fogging. Preferably, vents 164 have a tortuous flow path to minimize the risk that physical contaminants contact the wearer. For example, vents 164 may be cut at an angle through the tapered side piece to permit air flow while blocking contaminants. Alternatively, the shield may have a double lens to prevent fogging.

Figure 17:
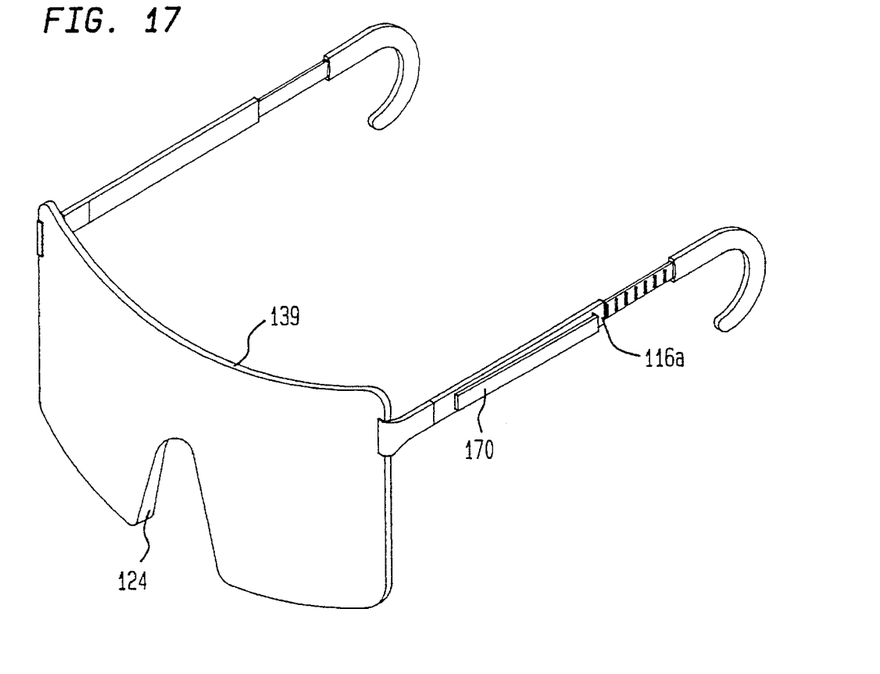
FIG. 17 is a perspective view of the invention showing another aspect of this invention.

The protective shield may also include a clip 170 as shown in FIG. 17. Clip 170 is rigidly attached at one end to temple bar 116a. This clip serves to externally affix the protective shield to an object, such as a garment of the wearer or a clipboard.

Figure 18:
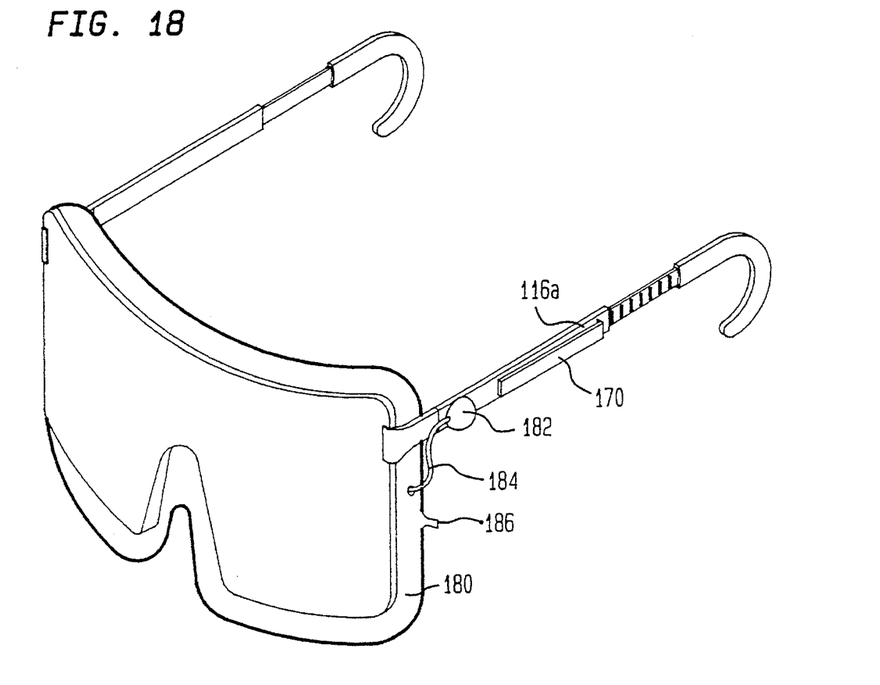
FIG. 18 is a perspective view of an eighth embodiment of the present invention.

According to an eighth embodiment of the present invention, the protective shield may also include a bladder 180 as shown in FIG. 18. This bladder preferably is easily inflatable and detachable, and is made of an autoclavable material. Bladder 180 surrounds the edges and periphery of main lens 135, and a hand pump 182 for inflating the bladder is in fluid communication with bladder 180 by way of conduit 184.

The bladder 180 may be conveniently positioned on or around the protective shield. As shown, bladder 180 is attached to temple bar 116a. The wearer may activate hand pump 182 until bladder 180 is of a size sufficient to contact the face and forehead of the wearer and to prevent the passage of contaminants from and to the wearer. The bladder can effectively seal the space between the protective shield and the wearer. Vents, such as vents 164, are particularly useful to prevent fogging when bladder 180 is used. Also, a valve 186 is provided on the bladder for deflation.

Although this invention has been described with reference to specific embodiments, it is not necessarily limited thereto. Accordingly, the appended claims should be construed to encompass not only those forms and embodiments of the invention specifically described above, but to such other forms and embodiments as may be devised by those skilled in the art without departing from its true spirit and scope.

What is claimed:

1. A device for protecting the eyes and surrounding area comprising:

two temple bars, each having at one end a curved ear piece adapted for resting on a wearer's ear:

a connecting bridge connecting each of the other ends of said temple bars and extending along the brow of the wearer and having holes formed said connecting bridge:

a nose support element extending downwardly from said connecting bridge and adapted for resting on the nose the wearer;

an outwardly extending projection bar having one end connected to said connecting bridge;

first coupling means connected to the other end of said projection bar;

a main lens coupled to said first coupling means;

first hinge means associated with said first coupling means for rotating said main lens;

second coupling means associated with said connecting bridge for coupling at least one interchangeable auxiliary lens to said connecting bridge and including mounting pins attached to said at least one auxiliary lens for engaging said holes formed on said connecting bridge; and second hinge means associated with said second coupling means for rotating said at least one auxiliary lens.

2. A device in accordance with claim 1 wherein said holes are formed on the inner face of said connecting bridge and said mounting pins include U-shaped ends for extending over a portion of said inner face and engaging said holes.

3. A device in accordance with claim 2 wherein said main lens has a narrow section and a widened top and said first coupling means includes a main recess which is shaped to form a channel for engaging said narrow section and said widened top of said main lens.

4. A device in accordance with claim 2 wherein said first coupling means includes a main recess, said main lens has a narrow section and a pointed top for pushing said main recess apart upon insertion of said main lens, and said main recess is shaped to form a channel for engaging said narrow section and said pointed top of said main lens.

5. A device in accordance with claim 2 wherein said temple bars include an inner edge and an outer edge, each having teeth in sliding engagement to adjust the length of said temple bars for a better fit to individual wearers.

6. A device in accordance with claim 5 wherein said temple bars include means for securing the desired adjustment of Said temple bars.

7. A device in accordance with claim 2 wherein said second hinge means includes a locking mechanism having an oblong nub with a protrusion adapted to engage recesses formed within said second hinge means.

8. A device in accordance with claim 7 wherein said second hinge means defines three recesses for locking said at least one auxiliary lens at angles of 0°, 90°, and 180° with respect to the downward facing vertical axis.

9. A device in accordance with claim 1 wherein said main and auxiliary lenses are curved.

10. A device in accordance with claim 1 further comprising means for adjusting the distance between said main lens and the wearer.

11. A device in accordance with claim 1 wherein said main lens is lightweight and scratch-resistant.

12. A device in accordance with claim 1 wherein said main lens includes means for correcting the vision of the wearer.

13. A device in accordance with claim 1 wherein said main lens includes means for filtering harmful radiation.

14. A device in accordance with claim 1 wherein said main lens is a magnification lens.

* * * * *

UNITED STATES PATENT AND TRADEMARK OFFICE
CERTIFICATE OF CORRECTION

PATENT NO. : 5,469,229
DATED : November 21, 1995
INVENTOR(S) : Steven S. Greenbaum It is certified that error appears in the above-indentified patent and that said Letters Patent is hereby corrected as shown below:

Column 3, line 20, delete "a-shield" and insert --a shield--.

Column 10, line 14, delete "formed said" and insert --formed on said--.

Column 10, line 56, delete "Said" and insert --said--.

Signed and Sealed this

Sixteenth Day of April, 1996

BRUCE LEHMAN

Attest:

Attesting Officer

Commissioner of Patents and Trademarks